US012629512B2

(12) United States Patent
Wah

(10) Patent No.: US 12,629,512 B2
(45) Date of Patent: May 19, 2026

(54) FEEDBACK CONTROL OF NEUROSTIMULATION

(71) Applicant: Saluda Medical Pty Ltd, Level (AU)

(72) Inventor: James Hamilton Wah, Artarmon (AU)

(73) Assignee: Saluda Medical Pty Ltd, Macquarie Park (AU)

( * ) Notice: Subject to any disclaimer, the term of this patent is extended or adjusted under 35 U.S.C. 154(b) by 574 days.

(21) Appl. No.: 18/023,341

(22) PCT Filed: Aug. 30, 2021

(86) PCT No.: PCT/AU2021/051001
§ 371 (c)(1),
(2) Date: Feb. 24, 2023

(87) PCT Pub. No.: WO2022/040758
PCT Pub. Date: Mar. 3, 2022

(65) Prior Publication Data
US 2023/0337962 A1 Oct. 26, 2023

(30) Foreign Application Priority Data

Aug. 28, 2020 (AU) ................................ 2020903082
Aug. 28, 2020 (AU) ................................ 2020903083

(51) Int. Cl.
*A61N 1/05* (2006.01)
*A61B 5/00* (2006.01)
(Continued)

(52) U.S. Cl.
CPC ............ *A61N 1/0551* (2013.01); *A61B 5/311* (2021.01); *A61B 5/388* (2021.01); *A61B 5/6847* (2013.01);
(Continued)

(58) Field of Classification Search
CPC .............. A61N 1/0551; A61N 1/36125; A61N 1/36139; A61N 1/36157; A61N 1/36067;
(Continued)

(56) References Cited

U.S. PATENT DOCUMENTS 5,913,882 A 6/1999 King
7,295,881 B2 11/2007 Cohen et al.
(Continued)

FOREIGN PATENT DOCUMENTS

DE 19758110 B4 7/2004
WO WO2006055849 A1 5/2006
(Continued)

OTHER PUBLICATIONS

Gorman et al., "Neural Recordings for Feedback Control of Spinal Cord Stimulation: Reduction of Paresthesia Variability", 2013, presented at the International Neuromodulation Society 11th World Congress, Berlin, Germany, 2 pgs.
(Continued)

*Primary Examiner* — Paula J Stice
(74) *Attorney, Agent, or Firm* — Barnes & Thornburg LLP

(57) ABSTRACT

Controlling a neural stimulus comprises applying the neural stimulus to a neural pathway in order to give rise to an evoked action potential on the neural pathway, the stimulus being defined by at least one stimulus parameter. A neural compound action potential response evoked by the stimulus is measured, and from the measured evoked response a feedback variable is derived. Loop backoff behaviour is adjusted by applying a non-identity function to the feedback variable to produce a revised feedback variable, and completing a feedback loop by using the revised feedback variable to control the at least one stimulus parameter so as to maintain the feedback variable at a setpoint. Additionally,
(Continued)

or alternatively, loop gain can be adjusted in response to a change in the loop setpoint, and/or a logarithm of the stimulus parameter can be controlled.

12 Claims, 7 Drawing Sheets

(51) Int. Cl.
    *A61B 5/311* (2021.01)
    *A61B 5/388* (2021.01)
    *A61N 1/36* (2006.01)

(52) U.S. Cl.
    CPC ..... *A61N 1/36125* (2013.01); *A61N 1/36139* (2013.01); *A61N 1/36157* (2013.01)

(58) Field of Classification Search
    CPC ........... A61N 1/36075; A61N 1/36062; A61N 1/36071; A61N 1/36132; A61B 5/311; A61B 5/388; A61B 5/1116
    See application file for complete search history.

(56) References Cited

U.S. PATENT DOCUMENTS

| | | | |
|---|---|---|---|
| 7,450,992 | B1 | 11/2008 | Cameron |
| 8,762,065 | B2 | 6/2014 | Dilorenzo |
| 9,205,263 | B2 | 12/2015 | King et al. |
| 9,302,112 | B2 | 4/2016 | Bornzin et al. |
| 9,387,325 | B1 | 7/2016 | Min et al. |
| 9,492,667 | B1 | 11/2016 | Kent et al. |
| 9,511,231 | B1 | 12/2016 | Kent et al. |
| 9,737,719 | B2 | 8/2017 | Skelton et al. |
| 9,907,960 | B2 | 3/2018 | Lian et al. |
| 9,950,171 | B2 | 4/2018 | Johanek et al. |
| 10,471,264 | B2 | 11/2019 | Bourget et al. |
| 10,842,996 | B2 | 11/2020 | Baru et al. |
| 11,090,493 | B2 | 8/2021 | Hou et al. |
| 11,259,732 | B2 | 3/2022 | Parramon et al. |
| 11,273,311 | B2 | 3/2022 | Su |
| 11,684,774 | B2 | 6/2023 | Crosby et al. |
| 11,786,725 | B2 | 10/2023 | Beck et al. |
| 2003/0153959 | A1 | 8/2003 | Thacker et al. |
| 2013/0165998 | A1 | 6/2013 | Libbus et al. |
| 2014/0277282 | A1 | 9/2014 | Jaax |
| 2019/0168000 | A1* | 6/2019 | Laird-Wah ........... A61B 5/0031 |
| 2019/0192855 | A1 | 6/2019 | Bharmi et al. |
| 2021/0345950 | A1 | 11/2021 | Annoni et al. |
| 2022/0054843 | A1 | 2/2022 | Carcieri |
| 2023/0067424 | A1 | 3/2023 | Crosby et al. |
| 2023/0241397 | A1 | 8/2023 | Parker et al. |
| 2023/0321438 | A1 | 10/2023 | Sachs et al. |
| 2023/0321439 | A1 | 10/2023 | Sachs et al. |

FOREIGN PATENT DOCUMENTS

| | | | |
|---|---|---|---|
| WO | WO2006017277 | A3 | 6/2006 |
| WO | WO2007064936 | A1 | 6/2007 |
| WO | WO2009015005 | A1 | 1/2009 |
| WO | WO2009046764 | A1 | 4/2009 |
| WO | WO2009051965 | A1 | 4/2009 |
| WO | WO2010080222 | A1 | 7/2010 |
| WO | WO2010088417 | A1 | 8/2010 |
| WO | WO2011112773 | A3 | 12/2011 |
| WO | WO2011159545 | A2 | 12/2011 |
| WO | WO2012155185 | A1 | 11/2012 |
| WO | WO2012155187 | A1 | 11/2012 |
| WO | WO2012155188 | A1 | 11/2012 |
| WO | WO2012155189 | A1 | 11/2012 |
| WO | WO2013063111 | A1 | 5/2013 |
| WO | WO2015031136 | A1 | 3/2015 |
| WO | WO2016057212 | A1 | 4/2016 |
| WO | WO2016057544 | A1 | 4/2016 |
| WO | WO2016090436 | A1 | 6/2016 |
| WO | WO2017173493 | A1 | 10/2017 |
| WO | WO2017184238 | A1 | 10/2017 |
| WO | WO2018063912 | A1 | 4/2018 |
| WO | WO2018080753 | A1 | 5/2018 |
| WO | WO2018089981 | A1 | 5/2018 |
| WO | WO2018152064 | A1 | 8/2018 |
| WO | WO2019027578 | A1 | 2/2019 |
| WO | WO2019067059 | A1 | 4/2019 |
| WO | WO2019070406 | A1 | 4/2019 |
| WO | WO2019136072 | A1 | 7/2019 |
| WO | WO2019177798 | A1 | 9/2019 |
| WO | WO2019190710 | A1 | 10/2019 |
| WO | WO2019204884 | A1 | 10/2019 |
| WO | WO2019190679 | A3 | 12/2019 |
| WO | WO2019246579 | A1 | 12/2019 |
| WO | WO2019246582 | A1 | 12/2019 |
| WO | WO2020047152 | A1 | 3/2020 |
| WO | WO2020206152 | A1 | 10/2020 |
| WO | WO2020243096 | A1 | 12/2020 |
| WO | WO2020251899 | A1 | 12/2020 |
| WO | WO2020257705 | A1 | 12/2020 |
| WO | WO2021030152 | A1 | 2/2021 |
| WO | WO2021080834 | A1 | 4/2021 |
| WO | WO2021080835 | A1 | 4/2021 |
| WO | WO2021080836 | A1 | 4/2021 |
| WO | WO2021126431 | A1 | 6/2021 |
| WO | WO2021126432 | A1 | 6/2021 |
| WO | WO2021126587 | A1 | 6/2021 |
| WO | WO2021126588 | A1 | 6/2021 |
| WO | WO2021162794 | A1 | 8/2021 |
| WO | WO2021162795 | A1 | 8/2021 |
| WO | WO2021178265 | A1 | 9/2021 |
| WO | WO2021211170 | A1 | 10/2021 |
| WO | WO2021252257 | A1 | 12/2021 |
| WO | WO2021262861 | A1 | 12/2021 |
| WO | WO2022010677 | A1 | 1/2022 |
| WO | WO2021255473 | A3 | 2/2022 |

OTHER PUBLICATIONS

Kent, "Characterization of Evoked Potentials During Deep Brain Stimulation in the Thalamus", 2013, Dissertation, Duke University. Retrieved from https://hdl.handle.net/10161/8195.

Laird-Wah, J., "Improving Spinal Cord Stimulation: Model-Based Approaches to Evoked Response Telemetry", UNSW Thesis, Aug. 2015, 279 pgs.

Parker et al., "Closing the Loop in Neuromodulation Therapies: Spinal Cord Evoked Compound Action Potentials During Stimulation for Pain Management (230)", Presented at the North American Neuromodulation Society, Las Vegas, 2011, In 15th Annual Meeting, North American Neuromodulation Society, p. 48.

* cited by examiner

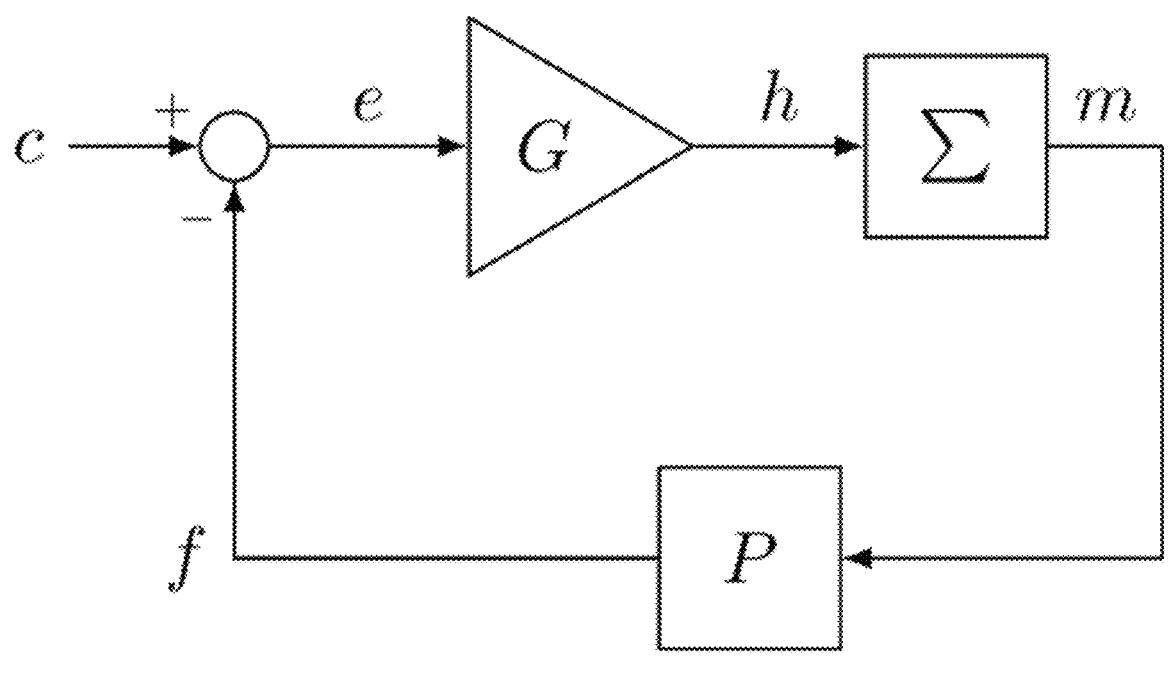
Figure 7
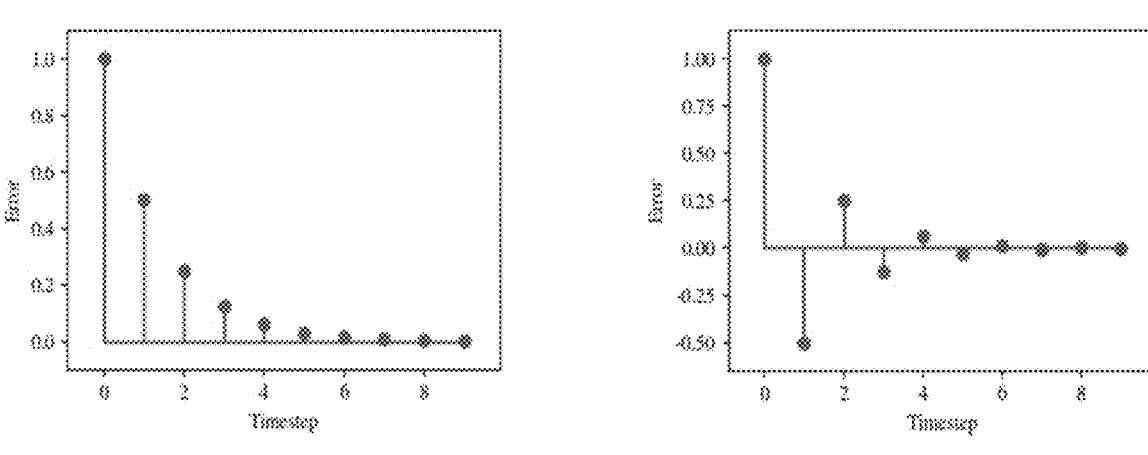
Figure 8                    Figure 9
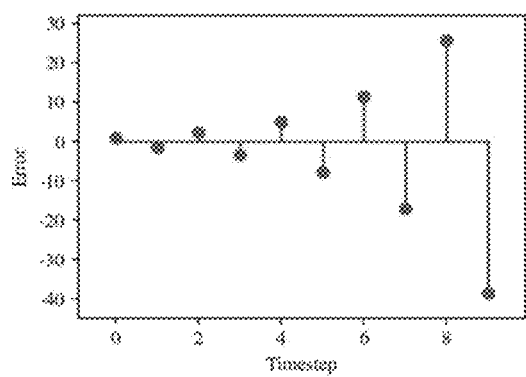
Figure 10

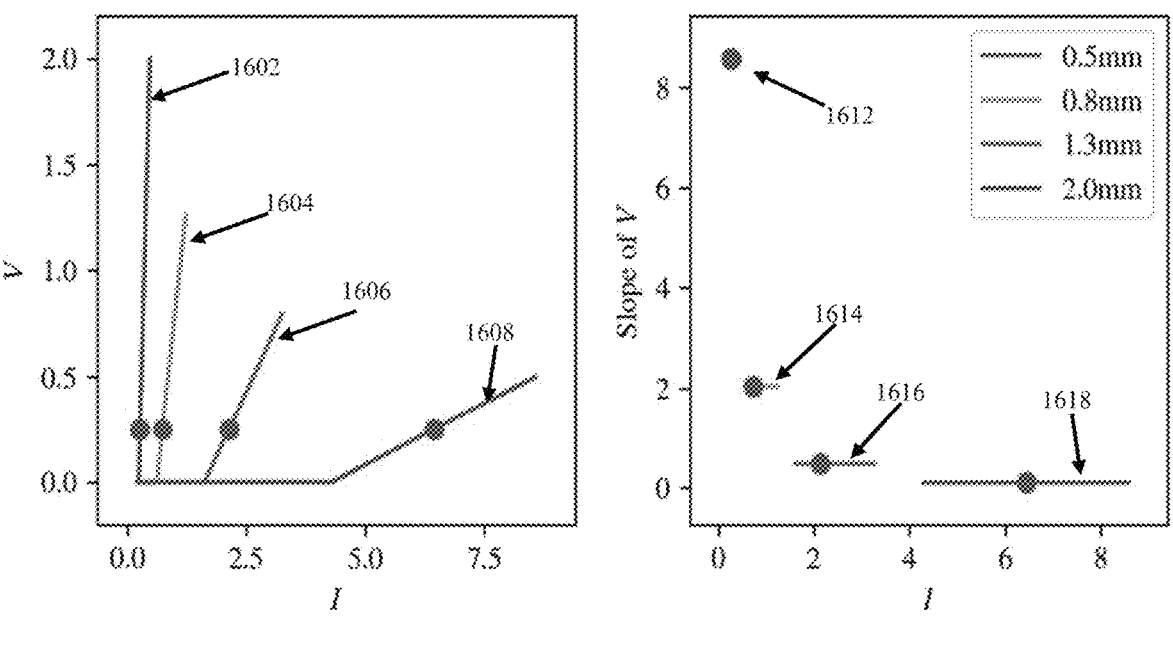
Figure 16a          Figure 16b
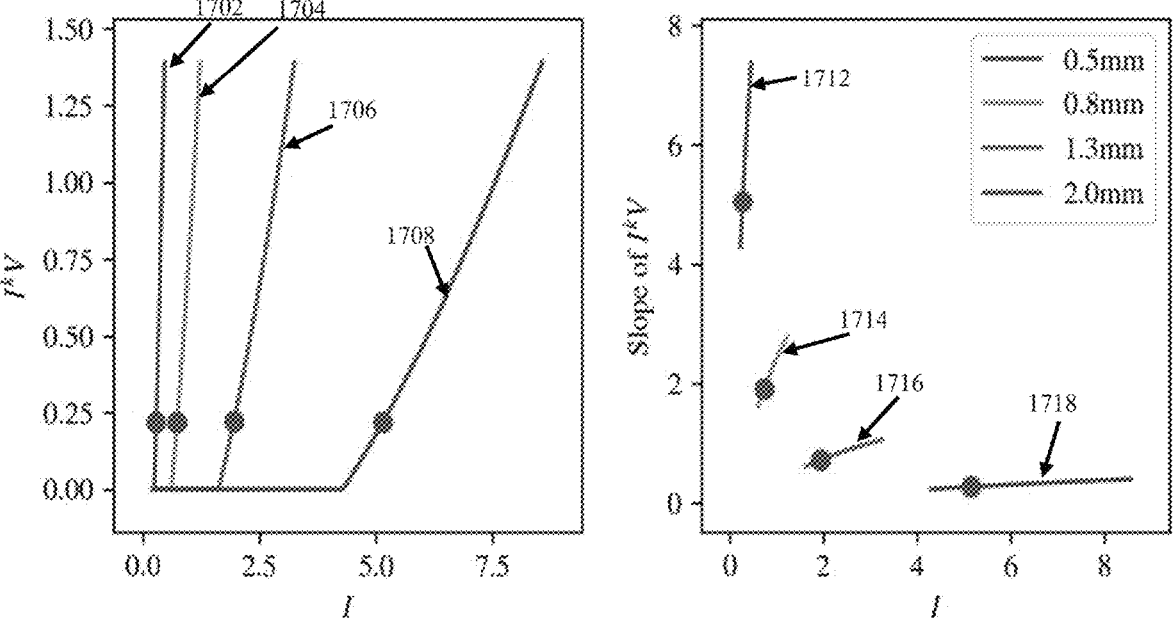
Figure 17a          Figure 17b

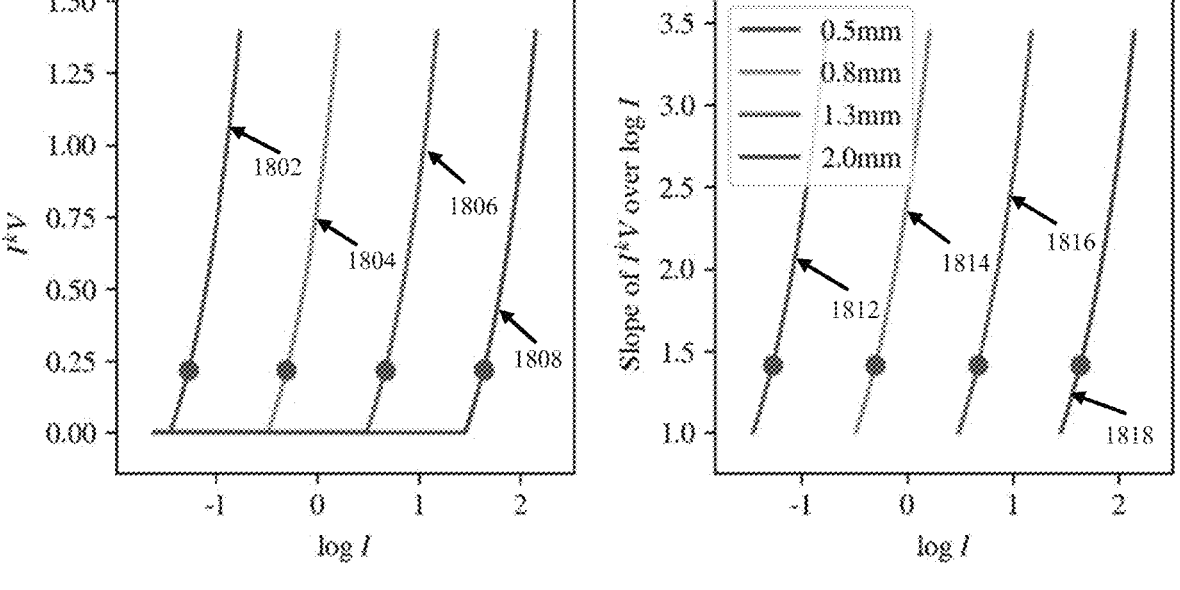
Figure 18a          Figure 18b

FEEDBACK CONTROL OF NEUROSTIMULATION

CROSS-REFERENCE TO RELATED APPLICATIONS

This application is a U.S. National Stage Patent Application of PCT Application No. PCT/AU2021/051001, filed Aug. 30, 2021, which claims the benefit of Australian Provisional Patent Application No. 2020903082 and Australian Provisional Patent Application No. 2020903083, both filed Aug. 28, 2020, both of which are incorporated herein by reference.

TECHNICAL FIELD

The present invention relates to controlling a neural response to a stimulus, and in particular relates to measurement of a compound action potential by using one or more electrodes implanted proximal to the neural pathway. This may be in order to improve feedback to control subsequently applied stimuli, and/or to assess impacts of postural changes.

BACKGROUND OF THE INVENTION

There are a range of situations in which it is desirable to apply neural stimuli in order to give rise to an evoked compound action potential (ECAP) and/or to alter neural function. For example, neuromodulation is used to treat a variety of disorders including chronic neuropathic pain, Parkinson's disease, and migraine. A neuromodulation system applies an electrical pulse to neural tissue in order to generate a therapeutic effect.

When used to relieve neuropathic pain originating in the trunk and limbs, the electrical pulse is applied to the dorsal column (DC) of the spinal cord, referred to as spinal cord stimulation (SCS). Such a system typically comprises an implanted electrical pulse generator, and a power source such as a battery that may be rechargeable by transcutaneous inductive transfer. An electrode array is connected to the pulse generator, and is positioned adjacent the target neural pathway(s). An electrical pulse applied to the neural pathway by an electrode causes the depolarisation of neurons, and generation of propagating action potentials. The fibres being stimulated in this way inhibit the transmission of pain from that segment in the spinal cord to the brain. To sustain the pain relief effects, stimuli are applied substantially continuously, for example at a frequency in the range of 30 Hz-100 Hz.

For effective and comfortable operation, it is necessary to maintain stimuli amplitude or delivered charge above a recruitment threshold. Stimuli below the recruitment threshold will fail to recruit any action potentials. It is also necessary to apply stimuli which are below a comfort threshold, above which uncomfortable or painful percepts arise due to increasing recruitment of Aβ fibres which when recruitment is too large produce uncomfortable sensations and at high stimulation levels may even recruit sensory nerve fibres associated with acute pain, cold and pressure sensation. In almost all neuromodulation applications, a single class of fibre response is desired, but the stimulus waveforms employed can recruit action potentials on other classes of fibres which cause unwanted side effects. The task of maintaining appropriate neural recruitment is made more difficult by electrode migration and/or postural changes of the implant recipient, either of which can significantly alter the neural recruitment arising from a given stimulus, depending on whether the stimulus is applied before or after the change in electrode position or user posture. There is room in the epidural space for the electrode array to move, and such array movement alters the electrode-to-fibre distance and thus the recruitment efficacy of a given stimulus. Moreover, the spinal cord itself can move within the cerebrospinal fluid (CSF) with respect to the dura. During postural changes the amount of CSF and the distance between the spinal cord and the electrode can change significantly. This effect is so large that postural changes alone can cause a previously comfortable and effective stimulus regime to become either ineffectual or painful.

Another control problem, facing neuromodulation systems of all types, is achieving neural recruitment at a sufficient level required for therapeutic effect, but at minimal expenditure of energy. The power consumption of the stimulation paradigm has a direct effect on battery requirements which in turn affects the device's physical size and lifetime. For rechargeable systems, increased power consumption results in more frequent charging and, given that batteries only permit a limited number of charging cycles, ultimately this reduces the implanted lifetime of the device.

Attempts have been made to address such problems by way of feedback, such as by way of the methods set forth in International Patent Publication No. WO 2012/155188 by the present applicant. Feedback seeks to compensate for nerve and/or electrode movement by controlling the delivered stimuli so as to maintain a constant ECAP amplitude. A functional feedback loop can also produce useful data for live operation and/or post-analysis, such as observed neural response amplitude and applied stimulus current, however device operation at tens of Hz over the course of hours or days quickly produces large volumes of such data which far exceed an implanted device's data storage capacities.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood that the element may be any one of the listed options, or may be any combination of two or more of the listed options.

SUMMARY OF THE INVENTION

According to a first aspect the present invention provides an implantable device for controllably applying a neural stimulus, the device comprising:

a plurality of electrodes including one or more stimulus electrodes and one or more sense electrodes;

a stimulus source for providing a stimulus to be delivered from the one or more stimulus electrodes to a neural pathway in order to give rise to an evoked action potential on the neural pathway;

measurement circuitry for recording a neural compound action potential signal sensed at the one or more sense electrodes; and a control unit configured to:

control application of a neural stimulus as defined by a stimulus parameter;

measure via the measurement circuitry a neural compound action potential response evoked by the stimulus;

determine from the measured evoked response and the stimulus parameter a feedback variable;

implement a feedback controller which completes a feedback loop, the feedback controller configured to use a control gain to control the stimulus parameter so as to maintain the feedback variable at a setpoint; and in response to a change in the setpoint, the control unit configured to adjust the control gain of the feedback controller.

According to a second aspect the present invention provides an automated method of controlling a neural stimulus, the method comprising:

applying the neural stimulus to a neural pathway in order to give rise to an evoked action potential on the neural pathway, the stimulus being defined by a stimulus parameter;

measuring a neural compound action potential response evoked by the stimulus, determine from the measured evoked response and the stimulus parameter a feedback variable;

completing a feedback loop by using a control gain to control the stimulus parameter so as to maintain the feedback variable at a setpoint; and adjusting, in response to a change in the setpoint, the control gain of the feedback controller.

In some embodiments of the first and second aspects the feedback controller is configured to control the stimulus parameter by calculating an error between the feedback variable and the setpoint; multiplying the error by the control gain to produce a multiplied error; and adjusting the stimulus parameter by the multiplied error. In some embodiments of the first and second aspects the control unit is configured to adjust the control gain of the feedback controller by calculating a slope of a control transfer function between the stimulus parameter and the feedback variable at the new setpoint; and adjusting the control gain in inverse proportion to the calculated slope. In some embodiments of the first and second aspects adjusting the control gain comprises dividing a predetermined open loop gain by the calculated slope.

According to a third aspect the present invention provides an implantable device for controllably applying a neural stimulus, the device comprising:

a plurality of electrodes including one or more stimulus electrodes and one or more sense electrodes;

a stimulus source for providing a stimulus to be delivered from the one or more stimulus electrodes to a neural pathway in order to give rise to an evoked action potential on the neural pathway;

measurement circuitry for recording a neural compound action potential signal sensed at the one or more sense electrodes; and a control unit configured to:

control application of a neural stimulus as defined by a stimulus parameter;

measure via the measurement circuitry a neural compound action potential response evoked by the stimulus;

determine from the measured evoked response a feedback variable;

apply a non-identity function to the feedback variable to produce a revised feedback variable, in order to adjust loop backoff behaviour; and implement a feedback controller which completes a feedback loop, the feedback controller configured to use the revised feedback variable to control the stimulus parameter so as to maintain the feedback variable at a setpoint.

According to a fourth aspect the present invention provides an automated method of controlling a neural stimulus, the method comprising:

applying the neural stimulus to a neural pathway in order to give rise to an evoked action potential on the neural pathway, the stimulus being defined by a stimulus parameter;

measuring a neural compound action potential response evoked by the stimulus, and deriving from the measured evoked response a feedback variable;

adjusting loop backoff behaviour by applying a non-identity function to the feedback variable to produce a revised feedback variable; and completing a feedback loop by using the revised feedback variable to control the stimulus parameter so as to maintain the feedback variable at a setpoint.

In some embodiments of the first to fourth aspects of the invention, the feedback variable comprises $C=I^kV$, where I is the stimulus current, V is a measure of the evoked response amplitude, and k is a ratio of an exponent m of a distance-dependent transfer function of stimulation to an exponent n of a distance-dependent transfer function of measurement. In such embodiments, the revised feedback variable may comprise $C'=C^q$, where q is selected to be $>1$ in order to increase a transfer function curvature, or is selected to be $<1$ in order to decrease a transfer function curvature. Alternatively, the revised feedback variable may comprise $C'=f(C)$, where $f$ is any non-linear function. For example, the non-linear function may comprise linear sections interposed by one or more non-linear kneepoints. The non-linear function may be effected by calculation on the fly or by any suitable look up table. The non-identity function may be a non-unity exponent.

In some embodiments of the first to fourth aspects of the invention, the non-identity function is configured so as to effect rapid back-off behaviour of the loop, such that, when the stimulus is under the target, the loop is configured to increase smoothly to converge to the target; and when the stimulus is over the target, the loop is configured to either decrease quickly to the target, or to overshoot down below the target and to then smoothly increase to converge to the target. Rapid back-off is considered desirable in neuromodulation to prevent overstimulation, and can be adjusted in this manner.

According to a fifth aspect the present invention provides an implantable device for controllably applying a neural stimulus, the device comprising:

a plurality of electrodes including one or more stimulus electrodes and one or more sense electrodes;

a stimulus source for providing a stimulus to be delivered from the one or more stimulus electrodes to a neural pathway in order to give rise to an evoked action potential on the neural pathway;

measurement circuitry for recording a neural compound action potential signal sensed at the one or more sense electrodes; and a control unit configured to:

control application of a neural stimulus as defined by a stimulus current parameter; measure via the measurement circuitry a neural compound action potential response evoked by the stimulus;

determine from the measured evoked response a feedback variable; and implement a feedback controller which completes a feedback loop, the feedback controller configured to use the feedback variable to control the logarithm of the stimulus current parameter so as to maintain the feedback variable at a setpoint.

According to a sixth aspect the present invention provides an automated method of controlling a neural stimulus, the method comprising:

applying the neural stimulus to a neural pathway in order to give rise to an evoked action potential on the neural pathway, the stimulus being defined by a stimulus current parameter;

measuring a neural compound action potential response evoked by the stimulus, and deriving from the measured evoked response a feedback variable; and completing a feedback loop by using the feedback variable to control the logarithm of the stimulus current parameter so as to maintain the feedback variable at a setpoint.

In some embodiments of the fifth and sixth aspects of the invention, a gain of the feedback loop is adjusted in response to changes in a setpoint of the feedback loop. Preferably, the gain is adjusted so as to ensure that loop dynamics are similar across setpoints. For example, a new value of gain may be calculated from an existing gain by dividing the existing gain by a value of a slope of an open loop transfer function at the new setpoint.

The logarithmic value of the stimulus current parameter may be determined as a base 10 logarithm of the stimulus current parameter. Alternatively, the logarithmic value of the stimulus current parameter may be determined as a natural logarithm, of base e, of the stimulus current parameter, or as any other suitable base logarithm.

The logarithmic value of the stimulus current parameter may be determined from the stimulus current parameter by calculation on the fly, or by reference to a lookup table, for example.

Embodiments of the fifth and sixth aspects may be particularly advantageous in providing improved stability of a non-linear neurostimulation feedback loop. When applied in relation to constant recruitment feedback loop control in particular, such embodiments may result in the loop being substantially insensitive to nerve-electrode distance.

In some embodiments the stimulus current parameter may comprise a stimulus current amplitude. In some embodiments the feedback variable may be determined from a measure of an observed ECAP amplitude, or a variable derived therefrom.

According to a further aspect the present invention provides a non-transitory computer readable medium for controllably applying a neural stimulus, comprising instructions which when executed by one or more processors carry out the method of the second or fourth or sixth aspect of the invention.

The neural stimulus may be defined by one stimulus parameter, such as by a stimulus current parameter, or may be defined by more than one stimulus parameter.

Maintaining the feedback variable at a setpoint may comprise maintaining neural recruitment at a constant level.

In embodiments of the fifth and sixth aspects, determining the feedback variable from the measured evoked response may comprise determining the feedback variable from the stimulus current parameter and from the measured evoked response. In such embodiments the feedback variable may then be used to control the stimulus current parameter.

The feedback variable could in some embodiments be determined from any one of: an amplitude; an energy; a power; an integral; a signal strength; or a derivative, of any one of: the whole evoked compound action potential; the fast neural response for example in the measurement window 0-2 ms after stimulus; the slow neural response for example in the measurement window 2-6 ms after stimulus; or of a filtered version of the response. The feedback variable could in some embodiments be determined from an average of any such variable determined over multiple stimulus/measurement cycles. The feedback variable may in some embodiments be determined from the zero intercept, or the slope, of a linear portion of the response of ECAP amplitude to varying stimulus current. In some embodiments the feedback variable may be derived from more than one of the preceding measures.

The neural recordings may in some embodiments be obtained in accordance with the teachings of the present Applicant for example in U.S. Pat. No. 9,386,934, International Patent Publication No. WO 2020/082118, International Patent Publication No. WO 2020/082126, and/or International Patent Publication No. WO 2020/124135, the content of each being incorporated herein by reference.

The feedback variable may be determined from the measured neural response by assessing the measured neural response to ascertain an amplitude of a second peak (e.g. an N1 peak) and/or an amplitude of a third peak (e.g. a P2 peak), for example by identifying an N1-P2 peak-to-peak amplitude, to produce the feedback variable.

In some embodiments of the invention, the measurement circuitry is configured to record the recordings of the neural responses substantially continuously during device operation. For example, in some embodiments of the invention the implanted neuromodulation device is configured to record the recordings of the neural responses for a period of at least 8 hours of device operation. In some embodiments of the invention the implanted neuromodulation device is configured to record the recordings of the neural responses for a period of at least 2 days of device operation. In some embodiments of the invention the implanted neuromodulation device is configured to record the recordings of the neural responses for a period of at least 5 days of device operation. To this end, preferred embodiments of the invention provide for the implanted neuromodulation device to be configured to process each recording of a neural response in substantially real time in order to obtain a respective measure of neural activation, and further provide for the implanted neuromodulation device to store in memory only the measure of neural activation and not the entire recording. For example, the implanted neuromodulation device may store in memory a histogram of the plurality of measures of neural activation in the form of a plurality of bins, with a counter associated with a respective bin being incremented each time an additional measure of neural activation is obtained. Such embodiments permit such data to be obtained over a period of hours or days at a high rate, such as at 50 Hz or more, and to be stored in very compact manner by use of a histogram and to thereby avoid exceeding the limited memory constraints and/or data transfer capacity of an implantable device. The bins may each be allocated a width, or range, which is equal for each bin. Alternatively, the bins may be allocated respective widths which increase with increasing levels of neural activation, such as linearly increasing bin widths or exponentially increasing bin widths.

References herein to estimation, determination, comparison and the like are to be understood as referring to an automated process carried out on data by a processor operating to execute a predefined procedure suitable to effect the described estimation, determination and/or comparison step(s). The approaches presented herein may be implemented in hardware (e.g., using digital signal processors, application specific integrated circuits (ASICS) or field programmable gate arrays (FPGAs)), or in software (e.g., using instructions tangibly stored on computer-readable media for causing a data processing system to perform the steps described herein), or in a combination of hardware and software. The invention can also be embodied as computer-readable code on a computer-readable medium. The computer-readable medium can include any data storage device that can store data which can thereafter be read by a computer system. Examples of the computer readable medium include read-only memory ("ROM"), random-access memory ("RAM"), magnetic tape, optical data storage device, flash storage devices, or any other suitable storage devices. The computer-readable medium can also be distributed over network coupled computer systems so that the computer readable code is stored and/or executed in a distributed fashion.

BRIEF DESCRIPTION OF THE DRAWINGS

An example of the invention will now be described with reference to the accompanying drawings, in which:

FIG. 7 illustrates a simplified model of an integrating control loop in one embodiment;

FIG. 8 illustrates a loop converging smoothly,

FIG. 9 illustrates a loop overshooting and converging; and

FIG. 10 illustrates a loop overshooting and diverging;

FIGS. 16a and 16b show the transfer functions for a simulated patient when constant-voltage feedback is employed;

FIGS. 17a and 17b show the transfer functions for the simulated patient when I-V control feedback is employed;

FIGS. 18a and 18b show the transfer functions for the simulated patient when I-V control feedback using logarithmic current is employed.

DESCRIPTION OF THE PREFERRED EMBODIMENTS

Figure 1:
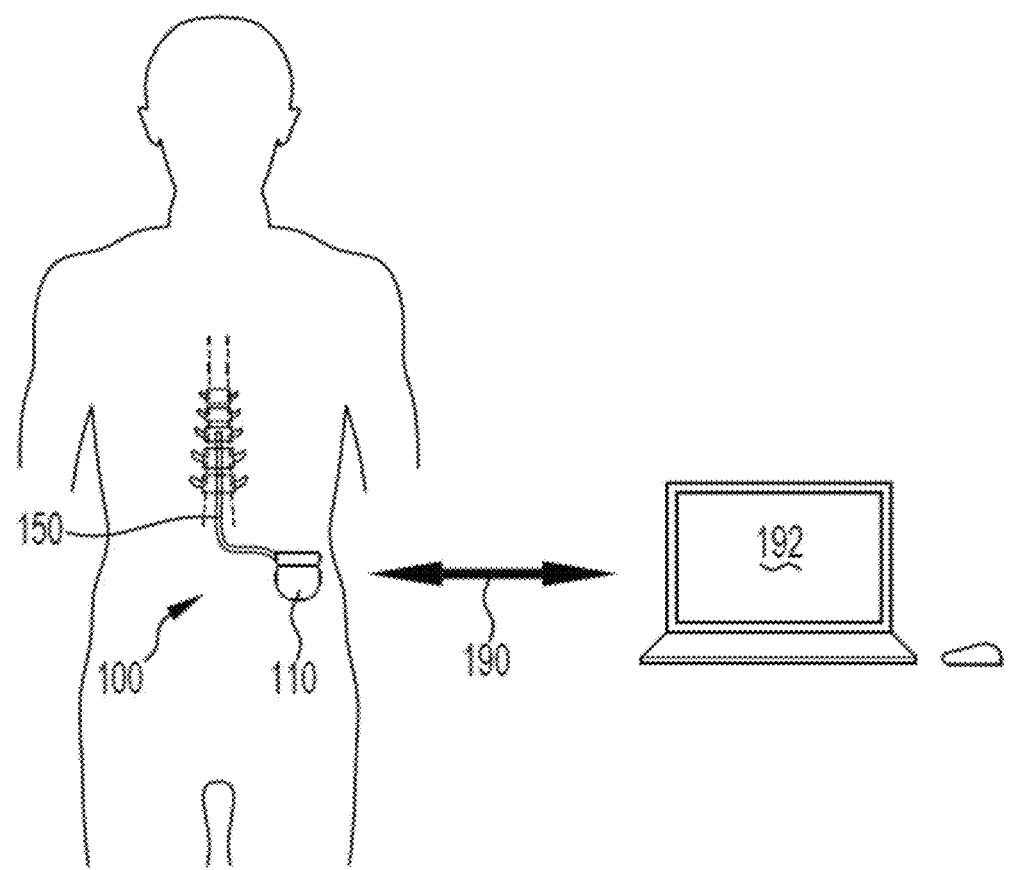
FIG. 1 schematically illustrates an implanted spinal cord stimulator.

FIG. 1 schematically illustrates an implanted spinal cord stimulator 100. Stimulator 100 comprises an electronics module 110 implanted at a suitable location in the patient's lower abdominal area or posterior superior gluteal region, and an electrode assembly 150 implanted within the epidural space and connected to the module 110 by a suitable lead. Numerous aspects of operation of implanted neural device 100 are reconfigurable by an external control device 192, which may be a clinician programmer and/or a patient programmer. Moreover, implanted neural device 100 serves a data gathering role, with gathered data being communicated to external device 192 via any suitable transcutaneous communications channel 190. Communications channel 190 may be effected by radio frequency (RF) communication, proximal inductive interaction or the like. Communications channel 190 may be active on a substantially continuous basis, at periodic intervals, at non-periodic intervals, or upon request from the external device 192.

Figure 2:
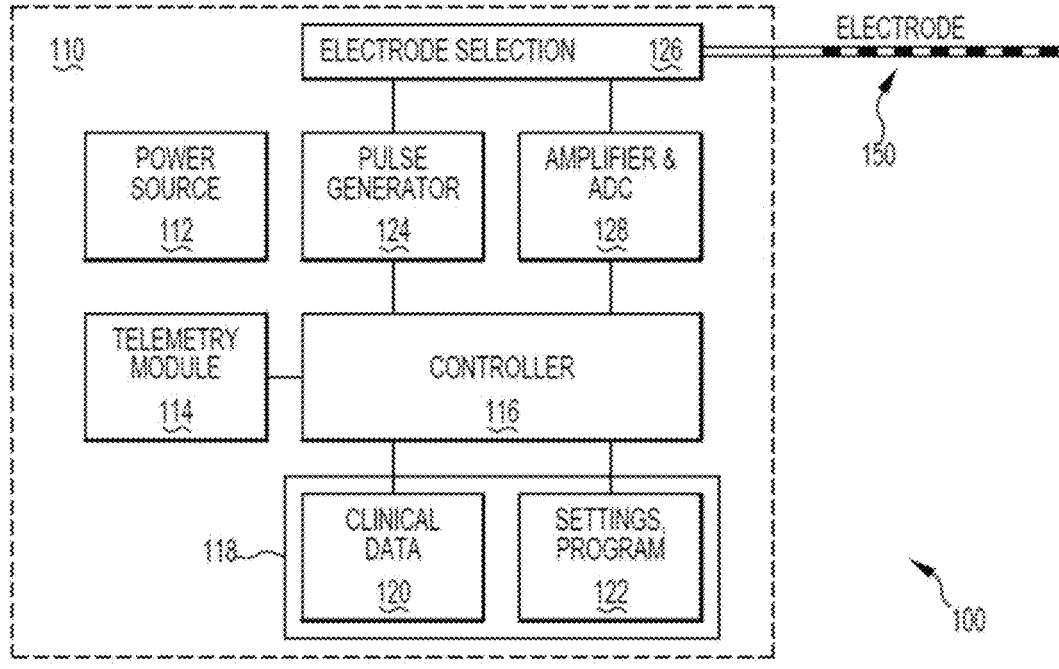
FIG. 2 is a block diagram of the implanted neurostimulator.

FIG. 2 is a block diagram of the implanted neurostimulator 100. Module 110 contains a battery 112 and a telemetry module 114. In embodiments of the present invention, any suitable type of transcutaneous communication 190, such as infrared (IR), electromagnetic, capacitive and inductive transfer, may be used by telemetry module 114 to transfer power and/or data between an external device 192 and the electronics module 110. Module controller 116 has an associated memory 118 storing patient settings 120, control programs 122 and the like. Controller 116 controls a pulse generator 124 to generate stimuli in the form of current pulses in accordance with the patient settings 120 and control programs 122. Electrode selection module 126 switches the generated pulses to the appropriate electrode(s) of electrode array 150, for delivery of the current pulse to the tissue surrounding the selected electrode(s). The electrode array 150 may comprise one or more electrodes such as electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for therapy. The electrodes may pierce or affix directly to the tissue itself. Measurement circuitry 128 is configured to capture measurements of neural responses sensed at sense electrode(s) of the electrode array as selected by electrode selection module 126.

Figure 3:
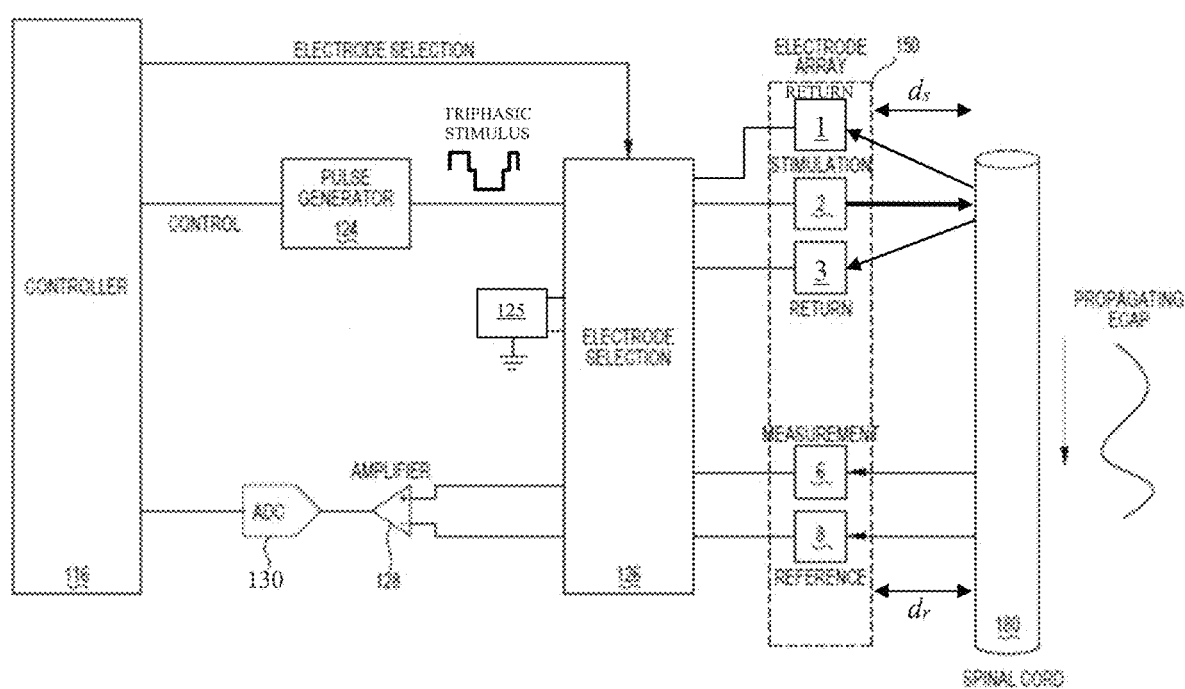
FIG. 3 is a schematic illustrating interaction of the implanted stimulator with a nerve.

FIG. 3 is a schematic illustrating interaction of the implanted stimulator 100 with a nerve 180, in this case the spinal cord however alternative embodiments may be positioned adjacent any desired neural tissue including a peripheral nerve, visceral nerve, parasympathetic nerve or a brain structure. Electrode selection module 126 selects a stimulation electrode 2 of electrode array 150 to deliver an electrical current pulse, which in this embodiment comprises three phases, i.e. a triphasic stimulus. The triphasic stimulus may be configured so as to reduce the effect of stimulus artefact upon ECAP measurements, in accordance with the teachings of WO 2017/219096, the contents of which are incorporated herein by reference. The electrode selection module 126 selects a stimulus electrode 2 to deliver the triphasic pulse to surrounding tissue including nerve 180, and also selects two return electrodes 1 and 3 of the array 150 for stimulus current recovery in each phase, to maintain a zero net charge transfer. The use of three electrodes in this manner for delivering and recovering current in each stimulus phase is referred to as tripolar stimulation. Stimulus current recovery is controlled by current return module 125. The tripolar stimulus may in some embodiments be configured in order to elicit a spatially constrained ECAP in accordance with the teachings of International Patent Publication No. WO 2020/082118, the contents of which are incorporated herein by reference. Additionally, or alternatively, the tripolar stimulus may be configured in order to minimise stimulus artefact so as to ease ECAP measurement in accordance with the teachings of International Patent Publication No. WO 2020/082126, the contents of which are incorporated herein by reference. Alternative embodiments may apply other forms of tripolar stimulation, or may use a greater or fewer number of stimulus electrodes.

Delivery of an appropriate stimulus from electrodes 1, 2, 3 to the nerve 180 evokes a neural response comprising an evoked compound action potential which will propagate along the nerve 180 as illustrated, for therapeutic purposes which in the case of a spinal cord stimulator for chronic pain might be to create paraesthesia at a desired location. To this end the stimulus electrodes are used to deliver stimuli at any therapeutically suitable frequency, for example 30 Hz, although other frequencies may be used including as high as the kHz range, and/or stimuli may be delivered in a non-periodic manner such as in bursts, or sporadically, as appropriate for the patient. To fit the device, a clinician applies stimuli of various configurations which seek to produce a sensation that is experienced by the user as a paraesthesia. When a stimulus configuration is found which evokes paraesthesia, which is in a location and of a size which is congruent with the area of the user's body affected by pain, the clinician nominates that configuration for ongoing use.

The device 100 is further configured to sense the existence and intensity of compound action potentials (CAPs) propagating along nerve 180, whether such CAPs are evoked by the stimulus from electrodes 1, 2 and 3, or otherwise evoked. To this end, any electrodes of the array 150 may be selected by the electrode selection module 126 to serve as measurement electrode 6 and measurement reference electrode 8, whereby the electrode selection module 126 selectively connects the chosen electrodes to the inputs of the amplifier 128. Thus, signals sensed by the measurement electrodes 6 and 8 are passed to the measurement circuitry comprising amplifier 128 and analog-to-digital converter (ADC) 130. The measurement circuitry for example may operate in accordance with the teachings of International Patent Publication No. WO 2012/155183 by the present applicant, the content of which is incorporated herein by reference.

Neural recordings obtained from the measurement electrodes 6, 8 via measurement circuitry 128, 130 are processed by controller 116 to obtain information regarding the effect of the applied stimulus upon the nerve 180. Stimulator 100 applies stimuli over a potentially long period such as days, weeks or months and during this time records neural responses, stimulation settings, paraesthesia target level, and other operational parameters. The stimulator 100 operates on a closed loop basis, in that the recorded neural responses are used in a feedback arrangement to control stimulation settings of future stimuli on a continuous or ongoing basis. To effect suitable SCS therapy stimulator 100 may deliver tens, hundreds or even thousands of stimuli per second, for many hours each day. The feedback loop may operate for most or all of this time, by obtaining neural response recordings following every stimulus, or at least obtaining such recordings regularly. Each recording generates a feedback variable such as a measure of the amplitude of the evoked neural response, which in turn results in the feedback loop changing the stimulation parameters for a following or later stimulus. Stimulator 100 thus may produce such data at a rate of tens or hundreds of Hz, or even kHz, and over the course of hours or days this process results in large amounts of clinical data which may be stored in the clinical data store 120 of memory 118. This is unlike past neuromodulation devices such as SCS devices which lack any ability to record any neural response. Memory 118 is however necessarily of limited capacity and care is thus required to select compact data forms for storage into the memory 118, to ensure that the memory is not exhausted before such time that the data is expected to be retrieved wirelessly by device 192, which may occur only once or twice a day, or less.

Accordingly, in the present embodiment the neural recordings produced by the measurement circuitry 128, 130 are processed by controller 116 in a manner which retrieves a single data point from each recording, comprising an ECAP peak-to-peak amplitude in μV. For example, the neural recordings may be processed to determine the ECAP peak-to-peak amplitude in accordance with the teachings of International Patent Publication No. WO 2015/074121, the contents of which are incorporated herein by reference. Alternative embodiments may select an alternative single data point to retrieve from the recording to be stored, or may retrieve and store 2 or more data points from the recording.

Figure 4:
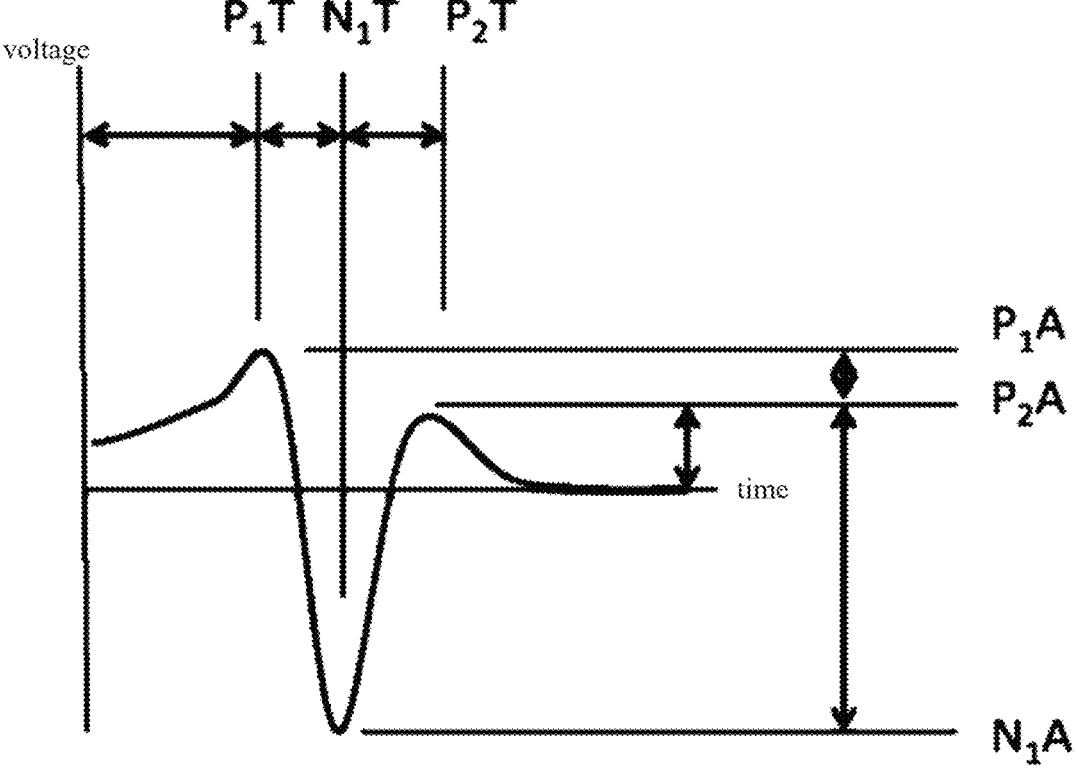
FIG. 4 illustrates the typical form of an electrically evoked compound action potential.

FIG. 4 illustrates the typical form of an electrically evoked compound action potential of a healthy subject. The shape of the compound action potential shown in FIG. 4 is somewhat predictable because it is a result of the ion currents produced by the ensemble of axons generating action potentials in response to stimulation. The action potentials generated among a large number of fibres sum to form a compound action potential (CAP). The CAP is the sum of responses from a large number of single fibre action potentials. The CAP recorded is the result of a large number of different fibres depolarising. The propagation velocity is determined largely by the fibre diameter. The CAP generated from the firing of a group of similar fibres is measured as a positive peak potential $P_1$, then a negative peak $N_1$, followed by a second positive peak $P_2$. This is caused by the region of activation passing the recording electrodes 6, 8 as the action potentials propagate along the individual fibres.

The CAP profile thus takes a typical form and can be characterised by any suitable parameter(s) of which some are indicated in FIG. 4. Depending on the polarity with which the recording electrodes 6, 8 are connected to amplifier 128, a normal recorded profile may take an inverse form to that shown in FIG. 4, i.e. having two negative peaks $N_1$ and N2, and one positive peak $P_1$.

As noted in the preceding, movement of the patient can cause the positions, shapes and alignments of the electrode array 150 and the nerve 180 to change considerably relative to each other and relative to the surrounding anatomy. In particular, as shown in FIG. 3, a distance $d_s$ of the stimulus electrode 2 from the nerve 180 can vary, as can a distance $d_r$ of the recording electrodes from the nerve 180. Due to flexibility of array 150 and nerve 180, and possible changes in the alignment and position of each, $d_s$ is not always equal to $d_r$, and changes in $d_s$ are not always equal to changes in $d_r$.

Figure 5:
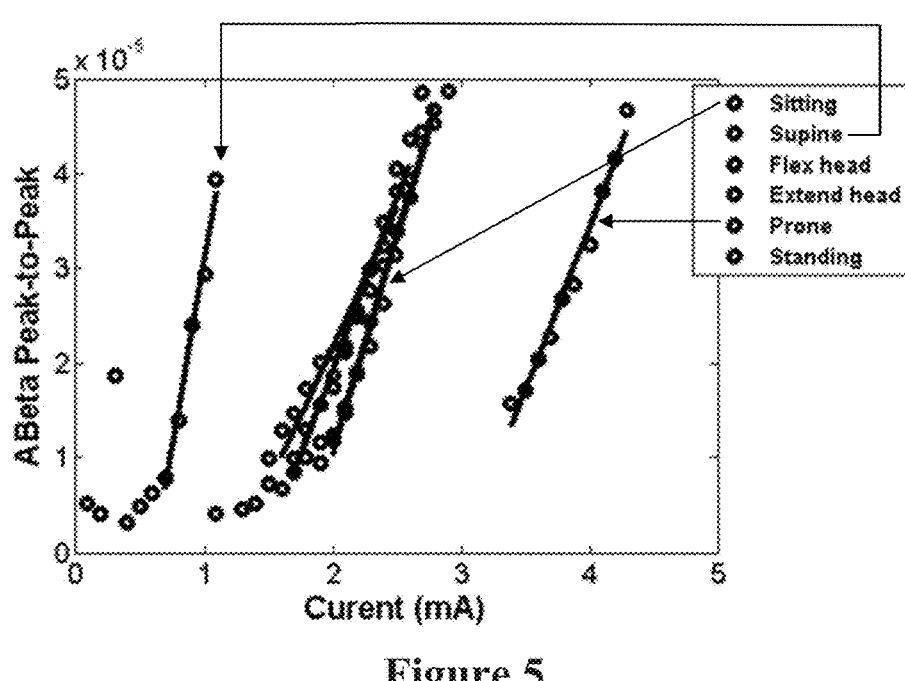
FIG. 5 illustrates a range of growth curves which may arise in a single patient, one for each posture.

At therapeutic levels, an observed CAP signal will typically have a maximum amplitude in the range of tens of microvolts. With increasing stimulus current I, the ECAP amplitude V typically follows a growth curve. FIG. 5 illustrates a range of growth curves which may arise in a single patient, one for each posture. A typical growth curve is characterised by a first portion below a threshold, in which a non-zero stimulus current elicits no ECAP, and a second portion above the threshold in which further increases in stimulus current above the threshold give rise to linearly increasing ECAP amplitude. The threshold T, and the slope M of the second portion of the growth curve, both depend on the electrode-to-fibre distance and thus both vary with posture. For example, as can be seen in FIG. 5, a supine posture has a lower threshold and a larger slope, as compared to a prone posture.

The present embodiment thus utilises a model of ECAP generation which accounts for situations where the electrodes move relative to the target tissue, as described in International Patent Publication No. WO 2017/173493, the contents of which are incorporated herein by reference. We revisit in the following some key elements of the model of ECAP generation, using slightly revised mathematical terminology.

The model of ECAP generation expresses a patient's transfer function from stimulus current, I, to ECAP amplitude, V. This transfer function depends on the cord-electrode distance, p, which itself depends on the patient's posture, and assuming here that $d_s = d_r = p$. The model depends only on the relative value of p, so we need to pick a reference point. We choose to set $p=1$ in the patient's reference posture. This could be any posture, preferably one the patient can easily repeat.

We use a piecewise linear model, where the ECAP increases linearly above threshold. The threshold T and slope M both vary with p:

$$V = \begin{cases} 0 & I < T(p) \\ M(p)(I - T(p)) & I \geq T(p) \end{cases}$$

T and M are dependent on the stimulus and recording transfer functions, which are assumed to be power laws. Let $T_0$ and $M_0$ be the threshold and slope, respectively, in the reference posture, ie.

$$T(1) = T_0$$

$$M(1) = M_0$$

For a suprathreshold current, the recruitment R effected by application of a stimulus falls off with the distance p, with some power m:

$$R \propto (I - T(p))p^{-m}$$

This is the stimulation transfer function.

Recording falls off with the distance p, with another power n:

$$V \propto Rp^{-n}$$

This is the recording transfer function.

From the above we get:

$$V = M_0 p^{-(m+n)}(I - T_0 p^m)$$

This is the patient's transfer function.

Thus we obtain the model functions:

$$T(p) = T_0 p^m$$

$$M(p) = M_0 p^{-(m+n)}$$

To effect a feedback loop which allows for both the stimulation transfer function as well as the recording transfer function in such a manner is referred to herein as I-V control. To implement I-V control we wish to maintain a constant recruitment, R, regardless of p. At constant recruitment:

$$I \propto p^m$$

$$V \propto p^{-n}$$

Constant recruitment here means stimulating at a constant multiple of the applicable threshold T(p). We can derive a feedback variable, C, so that the powers of p cancel:

$$C = I^n V^m$$

This has the property that:

$$\frac{dC}{dp} = 0$$

and so we can use C as a distance-independent measure of recruitment.

It is further to be noted that it is not necessary to know either m or n; we need only know their ratio, k, to derive a slightly different feedback variable:

$$k = \frac{n}{m}$$

$$C = I^k V$$

Figure 6:
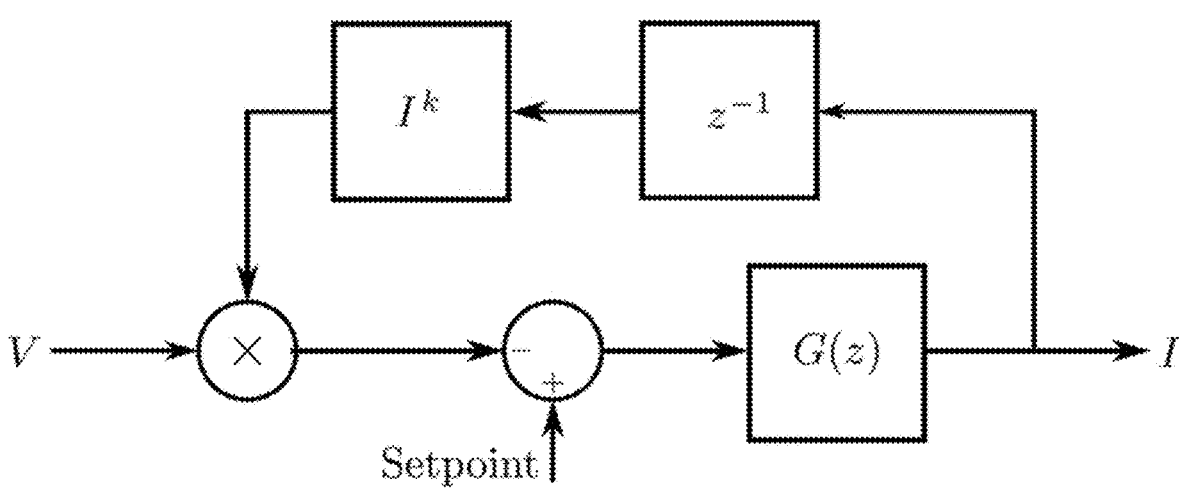
FIG. 6 illustrates application of a model of ECAP generation in a feedback loop, according to one implementation of I-V control of neurostimulation.

FIG. 6 illustrates application of such a model in a feedback loop, according to an original implementation of I-V control of neurostimulation.

This choice of C results in a control transfer function that curves upwards with increasing current, which is to say, $$\frac{d^2 C}{dI^2} > 0$$

which has beneficial implications for stability with an integrating controller, as is discussed herein in a later section on integrating control. This positive curvature means that the controller no longer has constant gain: when the setpoint is higher, the slope will be higher also. This can be compensated in the implementation by adjusting the control gain when the setpoint changes.

The value $I^k V$, or any monotonic function thereof, is a measure of the neural recruitment. This measure is not necessarily linear with the underlying recruitment, but it is monotonic.

The value of m will depend on the stimulation configuration; n will depend on the recording configuration. Both will also depend on lead placement and the patient's neural parameters. The value of k needs to be fitted to each patient configuration individually.

Accordingly, a fitting process is required. In this respect it is noted that the transfer parameter k can be determined without knowing p. Assuming that the patient's comfort level corresponds to a constant neural recruitment, one option is to use the patient's comfort level as a reference point. Under this approach, the current and voltage occurring at the patient's comfort level are measured in each of a plurality of postures. Let the comfort levels in the $i^{th}$ posture be denoted $V_i$ and $I_i$. Given that $$I_i \propto p_i^m$$
$$V_i \propto p_i^{-n}$$

we can simply fit a line through points $(\log I_i, \log V_i)$, which will have slope $-k$, yielding k for that particular patient.

Another fitting method is to look at the thresholds and slopes in different postures:

$$T_i = T_0 p^m$$
$$M_i = M_0 p^{-m} p^{-n}$$

A line through $(\log T_i, \log M_i T_i)$ would also have slope $-k$, thus providing another method by which to obtain the transfer parameter k for that particular patient.

The transfer parameter k can also be manually adjusted to fine-tune a patient's perceived uniformity. If they perceive an increase in stimulation when moving to a more sensitive posture, such as from prone to supine, then k should be decreased, and vice versa.

The feedback variable, $I^k V$, is a proxy for recruitment; it varies monotonically with recruitment regardless of posture, but it is a non-linear relationship. The present embodiment recognises that there are tasks where a linear measure of recruitment would be more useful: for example, for the patient to set their target level (setpoint), and for the analysis of feedback histograms.

When posture is held constant, the ECAP amplitude V varies roughly linearly with recruitment R, as in SCS the spatial extent of recruitment increases with current while the characteristics of the recruited population remain fairly constant with current.

Using the model equations, we can project any measurement of $I^k V$ on to any posture: this tells us what ECAP amplitude would be expected in that posture, for the same recruitment. This lets us define a linear recruitment measure, namely the equivalent ECAP amplitude in the reference posture, referred to herein as the refcap. The refcap, $\hat{V}$, has units of voltage.

The refcap is a natural choice of feedback variable for closed-loop control. The refcap also yields a measure of posture, independent of recruitment: the ratio $\hat{V}/V$ depends on $p^n$ but not R.

The refcap can be converted to and from the feedback variable, C, of the original implementation of I-V control by solving the equation $$C = \left(\frac{\hat{V}}{M_0} + T_0\right)^k \hat{V}$$

This equation has no closed-form solution, so a numeric method must be used to obtain the refcap $\hat{V}$ from the feedback variable C. The refcap may then be used as a feedback variable in a "refcap implementation" of I-V control of neurostimulation.

To calculate the refcap in an implant may be difficult as this requires heavy computation or lookup tables. On the other hand, it can be simple to estimate the posture when using the original implementation of I-V control. I-V control acts to keep the recruitment, and hence the refcap, constant. Thus, when using the original implementation of I-V control, the posture will vary with $V^{-1}$. Thus $V^{-1}$ yields an alternative posture estimate signal.

The refcap can be calculated regardless of the control method in use; k, $M_0$ and $T_0$ can be estimated in any patient, and used to calculate refcaps in open loop or constant voltage control modes as well as I-V control modes.

The present embodiments further provide for the integration of control of a nonlinear element in the feedback loop. An I-V feedback loop seeks to keep recruitment constant by adjusting the stimulus current. After each stimulus pulse, the ECAP is measured; the difference between the actual and desired feedback variable is the error. This error is multiplied by a control gain and then fed to an integrator. The integrator keeps a running sum of the errors to determine the next stimulus current. FIG. 7 illustrates a simplified model of the integrating control loop in this embodiment. The output of the integrator is the stimulus current m. The patient converts a stim current m into a feedback variable $f$ with some slope P. The difference between $f$ and the patient's setpoint, c, is the error, e. The loop error, e, is multiplied by gain G and integrated for the next time step.

In effect, after each stimulus, the system takes a step towards the desired setpoint. For example, if the measured ECAP is larger than the setpoint, the error is negative, and the integrator decreases the current. In implementing such a loop, it is important to understand the dynamic behaviour of the loop, such as how quickly it converges to the patient's setpoint, and under what circumstances might it become unstable and oscillate, and such behaviour is dictated by the step size. With a small step size, the loop converges smoothly towards the target. For example, FIG. 8 illustrates a loop converging smoothly when the open-loop gain is set to 0.5. On the other hand, if the steps are too large, the loop will overshoot the setpoint. FIG. 9 illustrates a loop overshooting but still converging, or ringing, where open loop gain is 1.5. FIG. 10 illustrates a loop overshooting and diverging, where open loop gain is 2.5; the loop is unstable.

Accordingly, preferred embodiments of the invention such as the embodiment of FIG. 7 provide an adjustable control gain G in the loop, to allow adjustment of the loop to suit each particular patient.

The step size of the loop depends on the open loop transfer function, h(m). This function captures what happens in the loop between the integrator's output and its input. In neurostimulation, since the patient's response throughout the therapeutic range is a straight line, the open loop transfer function is also a straight line. Thus the loop can be described just by its slope, the open loop gain. This is equal to the patient's growth curve slope P multiplied by the control gain G. This can be analysed using linear control theory. Using the z-transform, it can be demonstrated that the system is stable provided the open loop gain is less than 2. To further understand how the open-loop gain affects the loop dynamics, we provide the following reasoning from first principles.

The loop process begins by delivering a stimulus m and taking an ECAP measurement $f$, then calculating the error signal e. The integrator then takes a step in the direction of the setpoint, according to the product of the error and the control gain G. If the stimulus on step i is $m_i$, the feedback signal is $f_i = m_i P$, and the error is $e_i = c - m_i P$, and so the next stimulus current will be $$m_{i+1} = m_i + G(c - m_i P)$$

$$= Gc - m_i(1 - GP)$$

The convergence is seen by the progression of the error at the integrator, h:

$$h_{i+1} = (1 - GP)h_i$$

$$= (1 - A)h_i$$

where A is the total open-loop gain.

Figures 11, 12, 13, 14, 15:
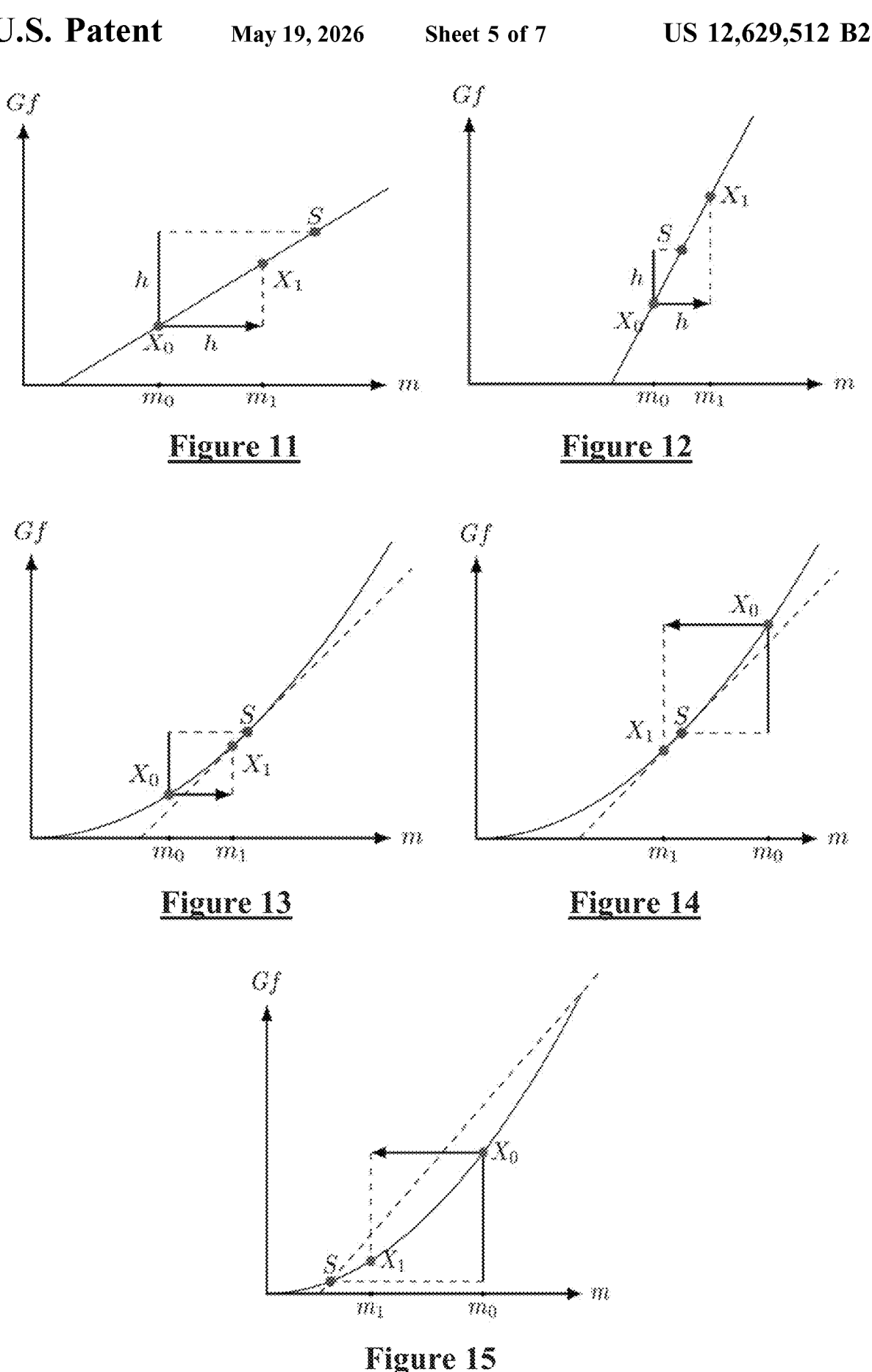
FIG. 11 illustrates an open-loop transfer function, showing one step of the loop update with A<1.
FIG. 12 illustrates an open-loop transfer function, showing one step of the loop update with A>1.
FIG. 13 illustrates a curved transfer function with slope A=1 at the setpoint S, showing one step of convergence from below.
FIG. 14 illustrates a curved transfer function with slope A=1 at the setpoint S, showing one step of convergence from above.
FIG. 15 illustrates a curved transfer function with slope A=⅓ at the setpoint S, showing one step of convergence from above.

This behaviour can also be understood geometrically by considering the open-loop transfer function. FIG. 11 illustrates the open-loop transfer function, showing one step of the loop update, with A<1. On these axes the line has slope A. The loop starts with current $m_0$, operating at point $X_0$. This results in gained error h, and the loop takes a step to $X_1$, resulting in new current $m_1$. In such cases, where the open-loop gain is less than 1, the change in m will be less than the distance from $X_0$ to the setpoint S. The next step will be smaller again; the process repeats and the system converges exponentially toward the setpoint. The time constant of this convergence is given by:

$$\tau = \frac{-1}{\log(1 - A)}$$

On the other hand, if the open-loop gain is greater than 1, the step is too big: the loop overshoots the setpoint. FIG. 12 illustrates the open-loop transfer function, showing one step of the loop update, with A>1. Again, the line has slope A. The loop starts with current $m_0$, operating at point $X_0$. This results in gained error h, and the loop takes a step to $X_1$, resulting in new current ml. On the next step, the loop will move back in the other direction; with that gain, it will overshoot again. In the case where 1<A<2, the system converges with time constant:

$$= \frac{-1}{\log(A - 1)}$$

This is almost identical to the A<1 case, with the difference being that the error alternates sign instead of converging from one side. This does result in a modulation of the stimulation, at half the loop frequency, which patients may find objectionable.

Thus the loop will settle fastest with A=1, becoming progressively slower as A increases or decreases, and becoming completely unstable for A>2.

As foreshadowed in the preceding, we now turn to the provision of the integration of control of a nonlinear element in the feedback loop. I-V control introduces non-linear elements into the loop: in one implementation, the feedback variable, $f$, is calculated as $I^k V$, so $f$ is no longer linear with respect to the stimulus parameter m. The open-loop transfer function with this formulation is still monotonic, and its slope is also monotonic; the transfer function always gets steeper at higher currents. In other words, the transfer function is curved upward. This behaviour can again be understood from a geometric perspective. A vertical error of h results in a horizontal step of the same size, h. If we draw a line at 45 degrees through the setpoint, we can deduce the next state: if the present state is above the line, the new state will be to the left of the setpoint, and vice versa.

If we choose G such that A=1 at the setpoint, all states below the setpoint are above the line $Gf=m$. Whenever the system state is below the setpoint, all successive states will be to the left, and it will converge smoothly from that side. FIG. 13 illustrates a curved transfer function with slope A=1 at the setpoint S. One step is taken from a state $X_0$ below the setpoint. A dashed line shows the 45 degree ($Gf=m$) boundary from the setpoint.

On the other hand, if the system is in a state $X_0$ above the setpoint S, it will take one step past the setpoint, shifting to state $X_1$ which is on the left side of S. FIG. 14 illustrates this eventuality. Thereafter it will converge smoothly from below the setpoint S, in the manner shown in FIG. 13. With a pure integrating controller, and the transfer function inflected (curved) upwards, it is sufficient to ensure A≤1 at the setpoint for the system to be stable.

In practice, embodiments of the invention are generally operated with A<1 at the setpoint S, for example due to a noise bandwidth specification. In such embodiments, there will exist a region above the setpoint S where system states will converge smoothly from above; this region is bounded by the intersection of the transfer curve with the line $Gf=m$. FIG. 15 illustrates a curved transfer function with slope A=⅓ at the setpoint. When one step is taken from a point $X_0$ above the setpoint S but below the intersection of the curve with the line $Gf=m$, the system will step to point $X_1$ which remains above S.

In further embodiments, when the I-V setpoint is changed, it may be desirable to adjust the controller gain, G, to maintain A at the setpoint at a constant level. This would help ensure that the loop dynamics are similar across setpoints. This can be implemented as follows: when the setpoint is changed, the slope of the control transfer function at the new setpoint is calculated, P, and the controller gain is immediately changed to G=A/P. Then the loop settles to the new value. Once again we can work out how this would behave from the geometric model. If the setpoint is increased, the controller gain will be decreased; the system state converges smoothly from below. If the setpoint is decreased, the controller gain is increased: what happens next depends on whether the current system state is above or below the intersection of the curve with the 45-degree line through the setpoint ($Gf=m$). If below, the system will converge smoothly from above. If above, the system will jump to a point below the setpoint, and then converge smoothly from below.

If a patient's target is stepped down significantly, and the gain is immediately updated for the new setpoint, the patient may experience an overshoot to a lower current than desired, before increasing to the desired level. This effect does not occur when the target is increased, as the above analysis shows there is overstimulation overshoot scenario. If this is found to be undesirable, ramping of the target and/or gain may be used to prevent overshoot.

Some embodiments of the invention may further provide for adjusting loop backoff behaviour. In this respect it is noted that when the loop transfer function is curved upward, system states sufficiently far above the setpoint will result in an immediate jump to below the setpoint. This instant backoff behaviour depends on the curvature, corner/knee-point or other non-linearity, of the loop transfer function, and begins to occur at the point where the loop transfer function intersects $Gf=m$. This point of intersection can be adjusted by adjusting the curvature or kneepoint of the loop transfer function. For example, in the original implementation of I-V control, the control variable is:

$$C = I^k V$$

The curvature of the loop transfer function can be adjusted in many ways in such embodiments; for example, by applying a non-identity function such as a non-unity exponent to the control variable:

$$C' = C^q$$

where $q>1$ would increase the curvature, and hence lower the point at which backoff occurs; and $q<1$ would decrease the curvature, and hence increase the point at which backoff occurs.

As long as the new control transfer function $C'(I)$ remains monotonic, and the gain adjustment is correspondingly updated to maintain the desired slope at the setpoint, the stability of the system is unaffected.

In a further embodiment, the present invention provides for logarithmic control of stimulation current. This is found to be beneficial by noting the following. The dynamic performance of the feedback loop depends on the open-loop gain A, which consists of the controller gain multiplied by the patient's growth curve slope. Because the growth curve slopes differ between postures, A varies with posture. A higher A results in faster performance, but for $A>2$ the system becomes unstable. The gain also affects the noise bandwidths, whereby lower gain values reduce the effect of noise on the loop, which in turn affects the patient's perception. In practice, when A varies with posture it is prudent to choose the controller gain to suit the patient in their most sensitive posture. As a consequence, when the patient is in a less sensitive posture the loop will respond more slowly than may be preferred.

Ideally, the open loop gain would be identical across postures. To this end one option is to operate the feedback loop in the log domain, whereby instead of controlling the current I the control loop controls $J=\log I$. This way, the loop takes larger current steps when the control variable is larger, typically corresponding to postures where the cord is less sensitive. It is to be noted that in previous approaches such as constant-voltage feedback, while log-domain control reduces the change in slope between postures, it also makes the slope dependent on the setpoint which complicates such approaches. However, in I-V control, where the slope in any event already depends on the setpoint, the control of logarithmic current is a highly beneficial approach because it completely eliminates variation in slope with posture, as demonstrated in more detail in the following.

This is most easily demonstrated graphically. To this end a simulated patient was created with $n=1.0$, $m=2.1$ to obtain $k=0.48$, as has been found by the inventors to be a realistic example. An arbitrary setpoint was chosen for both the previous approach of constant voltage feedback, and I-V control feedback, for plotting purposes. The patient was simulated at cord-electrode distances from $x=0.5$ mm to $x=2.0$ mm. The plots are presented in terms of the control transfer function: from the stimulation current I to the controlled (feedback) variable, the controlled variable being V for constant voltage feedback (FIGS. 16a and 16b), or being $I^k V$ for I-V control feedback (FIGS. 17a and 17b).

FIGS. 16a and 16b show the control transfer functions for the simulated patient when constant-voltage feedback is employed. In particular, 1602 indicates the control transfer function for an electrode-to-fibre distance of 0.5 mm, 1604 indicates the control transfer function for an electrode-to-fibre distance of 0.8 mm, 1606 indicates the control transfer function for an electrode-to-fibre distance of 1.3 mm, and 1608 indicates the control transfer function for an electrode-to-fibre distance of 2.0 mm. The indicated point on each curve represents the patient's setpoint, which is a constant voltage. These transfer functions are readily identified as the growth curves of the patient in different postures (FIG. 16a). FIG. 16b plots the supra-threshold transfer function slope 1612, 1614, 1616, 1618 for each respective transfer function 1602, 1604, 1606, 1608. The transfer function slope varies more than tenfold between the extremes of posture (FIG. 16b). If the loop is configured for $A=0.2677$ in the most sensitive posture, as per the inventors' experience with devices operating at 60 Hz, this would correspond to a roughly tenfold change in loop time constant between posture extremes. The slopes for each posture are constant with stimulus current, as evidenced by each line 1612, 1614, 1616, 1618 in FIG. 16b being horizontal. Thus, changing the setpoint up or down does not change the effective A of the patient.

FIGS. 17a and 17b show the control transfer functions for the simulated patient when I-V control feedback is employed. In particular, 1702 indicates the control transfer function for an electrode-to-fibre distance of 0.5 mm, 1704 indicates the control transfer function for an electrode-to-fibre distance of 0.8 mm, 1706 indicates the control transfer function for an electrode-to-fibre distance of 1.3 mm, and 1708 indicates the control transfer function for an electrode-to-fibre distance of 2.0 mm. The indicated point on each curve represents the patient's setpoint, which is a constant value of C $(=I^k V)$. FIG. 17b plots the supra-threshold transfer function slope 1712, 1714, 1716, 1718 for each respective transfer function 1702, 1704, 1706, 1708. Again, a significant variation in slope with posture is evident (FIG. 17b), although the effect is somewhat reduced in comparison with constant voltage (FIG. 16b). This implies that the loop dynamics will advantageously be somewhat less variable between postures when using I-V control as compared to constant voltage control.

FIGS. 18a and 18b show the transfer functions for the simulated patient when I-V control feedback using logarithmic current is employed. In particular, 1802 indicates the control transfer function for an electrode-to-fibre distance of 0.5 mm, 1804 indicates the control transfer function for an electrode-to-fibre distance of 0.8 mm, 1806 indicates the control transfer function for an electrode-to-fibre distance of 1.3 mm, and 1808 indicates the control transfer function for an electrode-to-fibre distance of 2.0 mm. The indicated point on each curve represents the patient's setpoint, which is a constant value of C (=$I^k$V). FIG. 18 demonstrates the significant benefit of using logarithmic current as the controlled variable. FIG. 18*b* plots the supra-threshold transfer function slope 1812, 1814, 1816, 1818 for each respective transfer function 1802, 1804, 1806, 1808. As can be seen in FIG. 18*b*, the control transfer function slope is completely independent of posture, i.e. is identical in every posture. This means that one loop gain value can be optimal for all postures, and that the loop dynamics will advantageously remain completely unchanged when the patient moves or changes posture.

Even so it is to be noted that the exact slope at the setpoint determines the loop dynamics. As can be seen from the slope curves in FIG. 18*b*, any change of setpoint will result in a different slope; this is true of I-V control with linear current as well as I-V control with logarithmic current. However, this can be addressed by adjusting the controller gain as the patient changes their setpoint, as discussed in the preceding.

The sensing and measurement of the ECAP signals are described in relation to the spinal cord, for example in the thoracic, thoracolumbar or cervical regions. In other embodiments the stimuli may be applied to, and/or ECAPs may be recorded in, other locations besides the spinal cord, such as peripheral nerves, or within the brain.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not limiting or restrictive.

The invention claimed is:

1. An implantable device for controllably applying a neural stimulus, the device comprising:
   a plurality of electrodes including one or more stimulus electrodes and one or more sense electrodes;
   a stimulus source for providing a neural stimulus to be delivered from the one or more stimulus electrodes to a neural pathway in order to give rise to an evoked compound action potential on the neural pathway of a patient;
   measurement circuitry for recording a neural compound action potential signal sensed at the one or more sense electrodes; and
   a control unit configured to:
      control application of the neural stimulus as defined by a stimulus current parameter;
      measure via the measurement circuitry the compound action potential evoked by the neural stimulus;
      determine from the measured evoked compound action potential a feedback variable; and
      implement a feedback controller which completes a feedback loop, the feedback controller configured to use the feedback variable to control a logarithm of the stimulus current parameter so as to maintain the feedback variable at a setpoint.

2. The implantable device of claim 1, wherein the control unit is configured to control the logarithm of the stimulus current parameter by:
   calculating an error between the feedback variable and the setpoint;
   multiplying the error by a control gain to generate a multiplied error; and
   adjusting the logarithm of the stimulus current parameter by the multiplied error.

3. The implantable device of claim 1, wherein the control unit is further configured to, in response to a change in the setpoint, adjust the control gain of the feedback controller.

4. The implantable device of claim 3, wherein the control unit is configured to adjust the control gain of the feedback controller by:
   calculating a slope of a control transfer function between the stimulus current parameter and the feedback variable at the changed setpoint; and
   adjusting the control gain in inverse proportion to the calculated slope.

5. The implantable device of claim 4, wherein the adjusting the control gain comprises dividing a predetermined open loop gain by the calculated slope.

6. The implantable device of claim 1, wherein the stimulus current parameter comprises a stimulus current amplitude.

7. The implantable device of claim 1, wherein the feedback variable is determined from a measure of an amplitude of the evoked compound action potential.

8. The implantable device of claim 1, wherein the feedback variable is determined from the stimulus current parameter.

9. The implantable device of claim 8, wherein the feedback variable comprises C=$I^k$V, where I is the stimulus current parameter, V is a measure of an amplitude of the evoked compound action potential, and k is a ratio of an exponent m of a distance-dependent transfer function of stimulation to an exponent n of a distance-dependent transfer function of measurement.

10. The implantable device of claim 8, wherein the feedback variable comprises an amplitude of a measured evoked compound action potential that would be obtained from the neural stimulus if the patient were in a reference posture.

11. An automated method of controlling a neural stimulus, the method comprising:
   applying the neural stimulus to a neural pathway in order to give rise to an evoked compound action potential on the neural pathway, the neural stimulus being defined by a stimulus current parameter;
   measuring a compound action potential evoked by the neural stimulus, and deriving from the measured evoked compound action potential a feedback variable; and
   completing a feedback loop by using the feedback variable to control a logarithm of the stimulus current parameter so as to maintain the feedback variable at a setpoint.

12. A non-transitory computer readable medium for controllably applying the neural stimulus, comprising instructions which when executed by one or more processors carry out the method of claim 11.

* * * * *